(12) United States Patent
Wang et al.

(10) Patent No.: US 8,785,412 B2
(45) Date of Patent: Jul. 22, 2014

(54) METHOD FOR INDUCING CANCER CELL APOPTOSIS OR INHIBITING THE CANCER CELL MIGRATION

(75) Inventors: Horng-Dar Wang, Hsinchu (TW); Chiou-Hwa Yuh, Hsinchu (TW); Shih-Ci Ciou, Hsinchu (TW); Yu-Ting Chou, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 85 days.

(21) Appl. No.: 13/195,143

(22) Filed: Aug. 1, 2011

(65) Prior Publication Data

US 2012/0258116 A1 Oct. 11, 2012

(30) Foreign Application Priority Data

Apr. 8, 2011 (TW) .............................. 100112343 A

(51) Int. Cl.
*C12N 15/11* (2006.01)

(52) U.S. Cl.
USPC ........................................................ 514/44 A

(58) Field of Classification Search
USPC .......................................................... 514/44 A
See application file for complete search history.

(56) References Cited

U.S. PATENT DOCUMENTS

2005/0123945 A1* 6/2005 Torres-Roca et al. ............. 435/6

OTHER PUBLICATIONS

Notice of Allowance of TW counterpart application No. 100112343 issued on Nov. 5, 2013 and its English translation.

* cited by examiner

*Primary Examiner* — Brian Whiteman
(74) *Attorney, Agent, or Firm* — WPAT, P.C.; Anthony King; Kay Yang

(57) ABSTRACT

The present invention is related to a method for inducing the cancer cell apoptosis or inhibiting the cancer cell migration by inhibiting the expression of ribose-5-phosphate isomerase A.

5 Claims, 33 Drawing Sheets

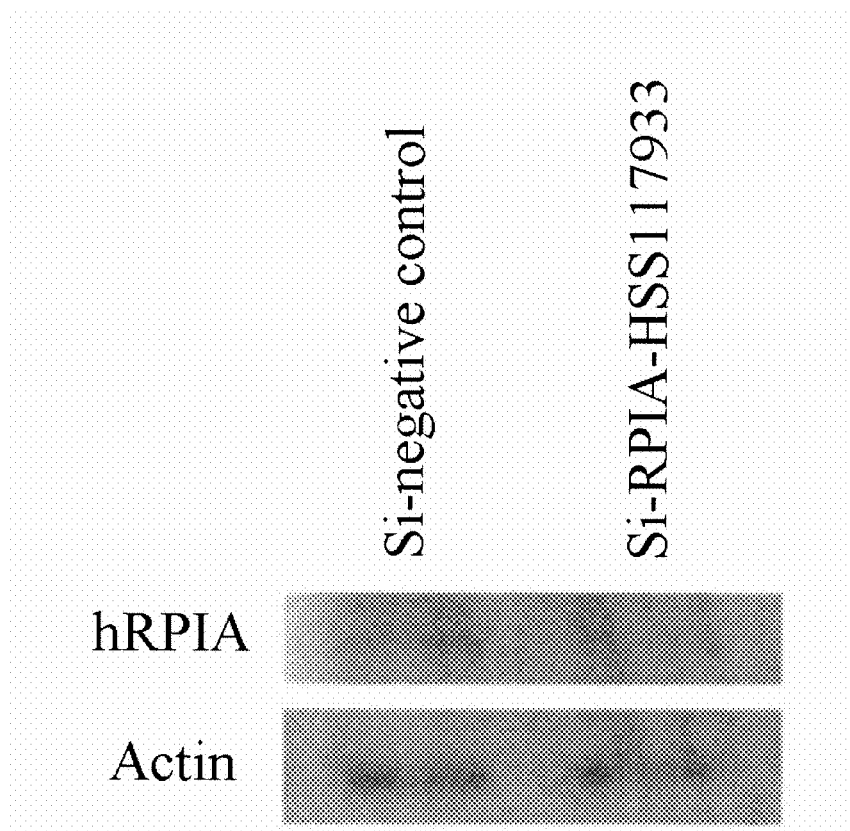
Fig. .4A

METHOD FOR INDUCING CANCER CELL APOPTOSIS OR INHIBITING THE CANCER CELL MIGRATION

CROSS-REFERENCE TO RELATED APPLICATIONS

This Non-provisional application claims priority under 35 U.S.C. §119(a) on Patent Application No(s). 100112343 filed in Taiwan, Republic of China Apr. 8, 2011, the entire contents of which are hereby incorporated by reference.

FIELD OF INVENTION

The present invention is related to a method for inducing the cancer cell apoptosis or inhibiting the cancer cell migration by inhibiting the expression of ribose-5-phosphate isomerase A.

BACKGROUND OF THE INVENTION

Cancer is the first leading cause of death and the liver cancer is the most lethal cancer along the years in Taiwan. The main cause of cancer is due to cell abnormal transformation or abnormal proliferation, wherein, a solid lesion formed by an abnormal growth of cells (termed neoplastic) which looks like a swelling is so called tumor. The tumor is classified as solid tumor and non-solid tumor. The solid tumor includes hepatic cancer, non-small cell lung cancer (NSCLC), colon cancer, melanoma, ovary cancer, prostate cancer, kidney cancer, breast cancer, gastric cancer, etc. Most of the non-solid tumors are hematologic malignancies which include leukemia, malignant lymphoma, etc. Recently, the rate of suffering from hepatic cancer and colon cancer is getting higher and higher. How to treat these cancers becomes a serious issue.

The research of aging has become a general focus in the whole world, and it is found that aging is associated with elevated oxidative stress and increased cancer risk. Cancer occurrence is positively correlated with the process of aging. Cancer and aging share some common mechanisms for their biological functions.

Pentose phosphate pathway (PPP) is an important cellular defense system against oxidative stress by removing excessive Reactive Oxygen Species (ROS) from mitochondrial oxidative phosphorylation. The major function of PPP is to generate NADPH to provide more reduced forms of glutathione counteracting the damaging effects of ROS.

Most cancers were found with increased activities of pentose phosphate pathway. Ribose-5-phosphate isomerase (RPI) is an enzyme involved in pentose phosphate pathway (PPP) to convert the ribulose-5-phosphate into ribose-5-phosphate wherein the ribose-5-phosphate is an important source of synthesis DNA and RNA in cells. Many researches show that RPI is involved in the aging pathway and the anti-oxidant pathway. However, there is no research shows that RPI can be used as an important index for cancer detection.

SUMMARY OF THE INVENTION

The present invention provides a method for inducing the cancer cell apoptosis by the way of inhibiting the expression of ribose-5-phosphate isomerase A in said cancer cell.

The invention also provides a method for inhibiting the cancer cell migration by the way of inhibiting the expression of ribose-5-phosphate isomerase A in said cancer cell.

As mentioned above, wherein said cell is solid cancer cell.

As mentioned above, wherein said solid cell is colon cancer cell or hepatic cancer cell.

As mentioned above, wherein the way of inhibiting the expression of ribose-5-phosphate isomerase A is to add a RNAi, siRNA or miRNA into said cancer cell or to knockdown a ribose-5-phosphate isomerase A (hRPIA) gene in said cell.

As mentioned above, wherein the way of inhibiting the expression of ribose-5-phosphate isomerase A is to add a small molecule, an antibody or a peptide into said cancer cell.

As mentioned above, wherein the way of inhibiting the expression of ribose-5-phosphate isomerase A is to add a RNAi, siRNA or miRNA into said cancer cell, the RNAi, siRNA or miRNA is the complementary sequence of ribose-5-phosphate isomerase A.

The invention further provides a method of enhancing the sensitivity of cancer cells for chemotherapeutic agents by inhibiting the expression of ribose-5-phosphate isomerase A in said cancer cell.

To summary briefly, the present invention provides a method for regulating the ribose-5-phosphate in cancer cell by inhibiting the expression or activity of ribose-5-phosphate isomerase A in said cell, so as to inhibit the migration of cancer cells or cancer tissues in the patient and to induce the cancer cell apoptosis or cancer tissue death to prevent and/or cure the cancer.

BRIEF DESCRIPTION OF THE DRAWINGS

FIG. 1 shows the mRNA level of hRPIA in HCC tissue and hepatic cancer cell line.

FIG. 2 shows the examination result of hRPIA protein level following hRPIA siRNA knockdown in hepatic cancer cells.

FIG. 3 shows the examination result of cell viability following hRPIA siRNA knockdown in hepatic cancer cells.

FIG. 4 shows the examination result of hRPIA protein level following hRPIA siRNA knockdown in colon cancer cells.

FIGS. 4A-B shows the knockdown of hRPIA with siRNA reduces hRPIA protein expression in SW480 (A) and SW620 (B) colon cancer cells in the western blot analysis. Actin was used as an internal control.

FIG. 5 shows the examination result of cell viability following hRPIA siRNA knockdown in colon cancer cells.

FIG. 6 shows the examination result of hRPIA protein level following hRPIA over-expression in hepatic cancer cells.

FIG. 7 shows the examination result of cell viability following hRPIA over-expression in hepatic cancer cells.

FIG. 8 shows the examination result of hRPIA protein level following hRPIA over-expression in colon cancer cells.

FIG. 9 shows the examination result of cell viability following hRPIA over-expression in colon cancer cells.

FIG. 10 shows the influence of chemotherapeutic agents following hRPIA siRNA knockdown in hepatic cancer cells.

FIG. 11 shows the influence of chemotherapeutic agents following hRPIA siRNA knockdown in colon cancer cells.

FIG. 14 shows the examination of caspase-3 and β-catenin protein level following hRPIA siRNA knockdown in hepatic cancer cells.

DETAILED DESCRIPTION OF THE INVENTION

To further illustrate the present invention, the following specific examples are provided.

EXAMPLES

Example 1

Examine the mRNA level of hRIPA in HCC tissue and cancer cells

To examine the expression level of human ribose 5-phosphate isomerase A (hRPIA) in the liver tumor biopsies from the cancer patients and cancer cell lines. The mRNA level of hRPIA was measured by real-time PCR in the liver tumors and normal liver tissues of the same HCC patients. The results are shown as FIG. 1A and FIG. 1B respectively.

When the mRNA level of hRPIA in each patient's liver cell is higher than in normal liver cell for 2-fold is defined as significantly increment; otherwise when the mRNA level of hRPIA in each patient's liver cell is lower than in normal liver cell for 0.5-fold is defined as significantly decrement.

Figure 1A:
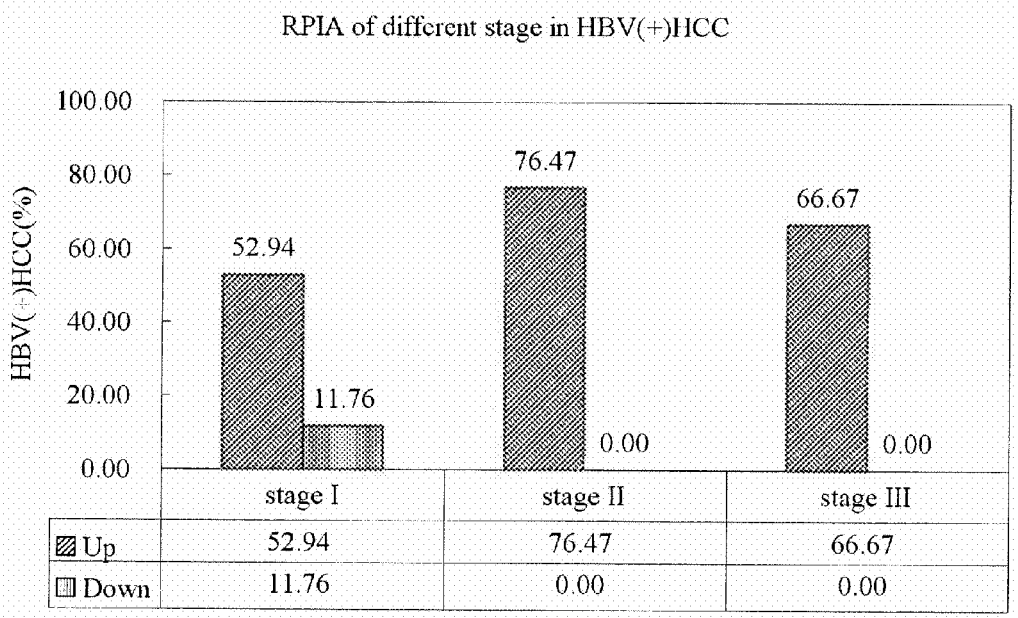
FIG. 1A shows significantly high percentage of HBV(+) HCC patients at different stages were detected increased (2-fold increase) hRPIA mRNA expression in their liver tumor tissues compared to the surrounding normal liver tissues. In the stage I—53% (n=17), II—76% (n=17), III—67% (n=15). n: patient number.
Figure 1B:
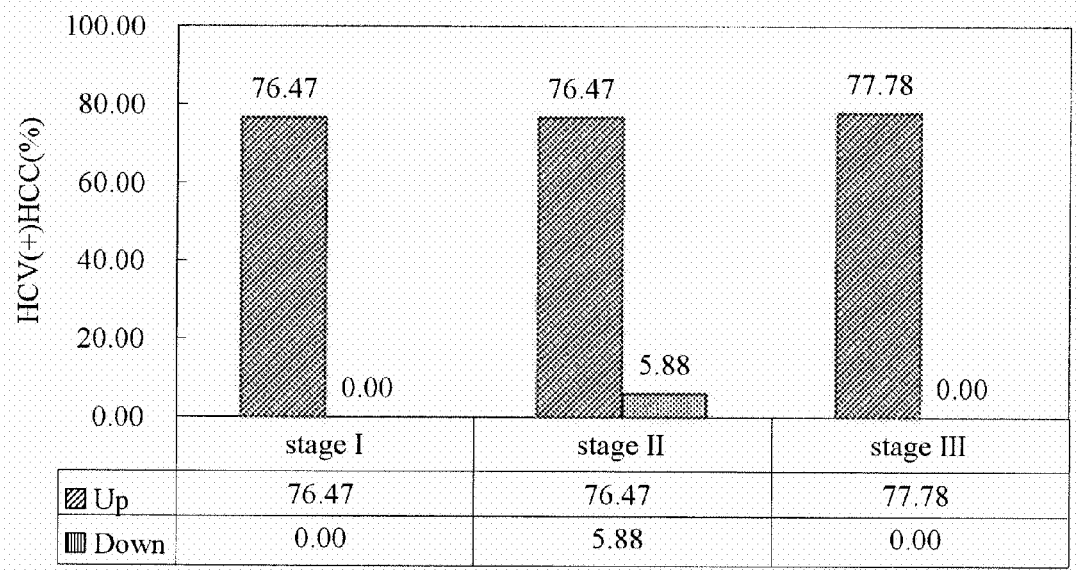
FIG. 1B shows significantly higher percentage of HCV(+) HCC patients at different stages were detected increased (2-fold increase) hRPIA mRNA expression in their liver tumor tissues compared to the surrounding normal liver tissues. In the stage I—76% (n=17), II—76% (n=17), III—78% (n=9). n: patient number.

As shown in FIG. 1A, in the stage I (n=17), II (n=17), III (n=15) of HBV-induced hepatocarcinoma, the average level of hRPIA gene expression was significantly higher in the tumor tissues than the normal liver tissues from HCC patients. A similar hRPIA mRNA expression patterns in stage I (n=17), II (n=17), III (n=9) of HCV-induced hepatocarcinoma were also obtained (FIG. 1B).

To summary briefly, the mRNA level of hRPIA in each patient's liver cell is higher than in normal liver cell.

Example 2

Examine the Cell Growth of Liver Cancer Cell after Knockdown of hRPIA

Figure 2A:
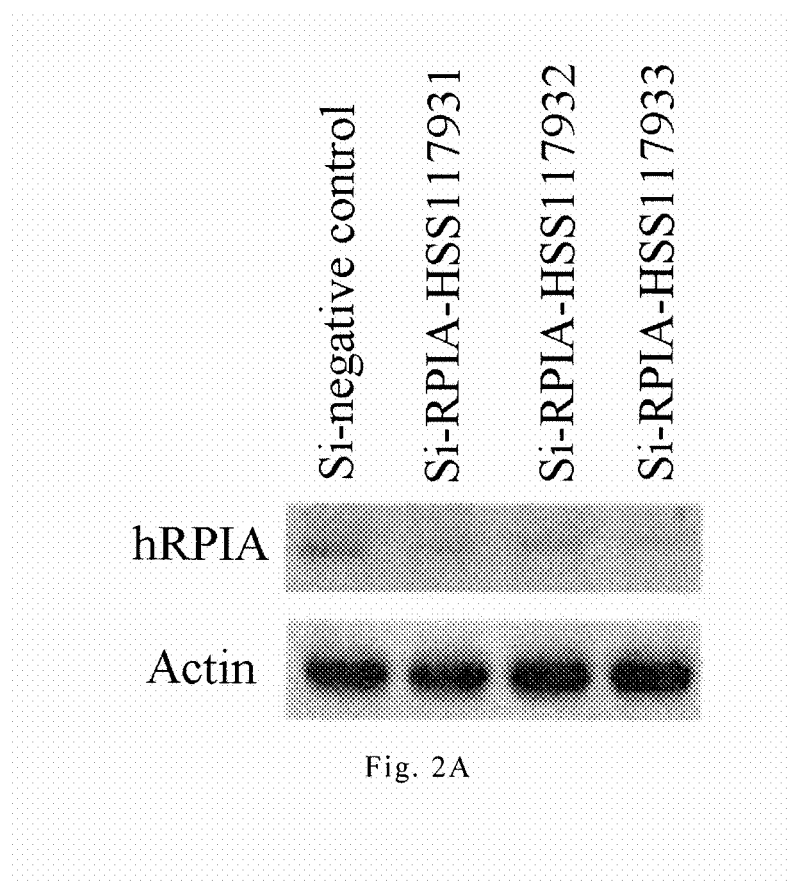
FIG. 2A shows the western blot analysis indicates that knockdown of hRPIA by three different siRNA, si-hRPIA-HSS117931, si-hRPIA-HSS117932, si-hRPIA-HSS117933 in Hep3B liver cancer cells results in decreased hRPIA protein expression (lane 2, 3, 4) compared to the control with si-negative control (lane 1). Actin was used as an internal control.
Figure 2B:
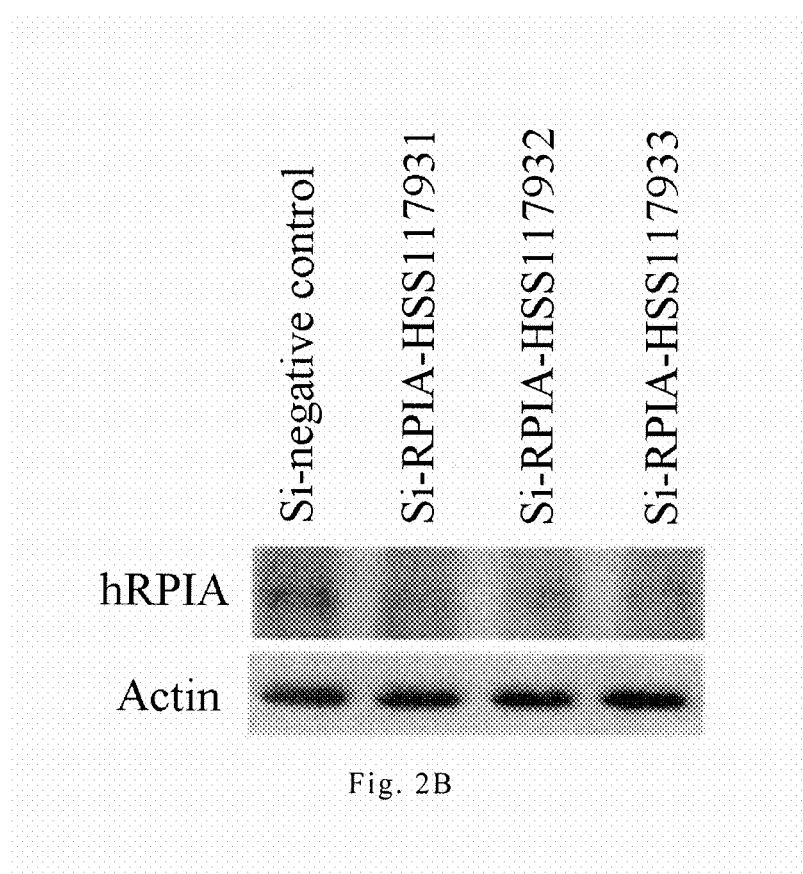
FIG. 2B shows the western blot analysis indicates that knockdown of hRPIA by three different siRNA, si-hRPIA-HSS117931, si-hRPIA-HSS117932, si-hRPIA-HSS117933 in PLC5 liver cancer cells results in decreased hRPIA protein expression (lane 2, 3, 4) compared to the control with si-negative control (lane 1). Actin was used as an internal control.
Figure 2C:
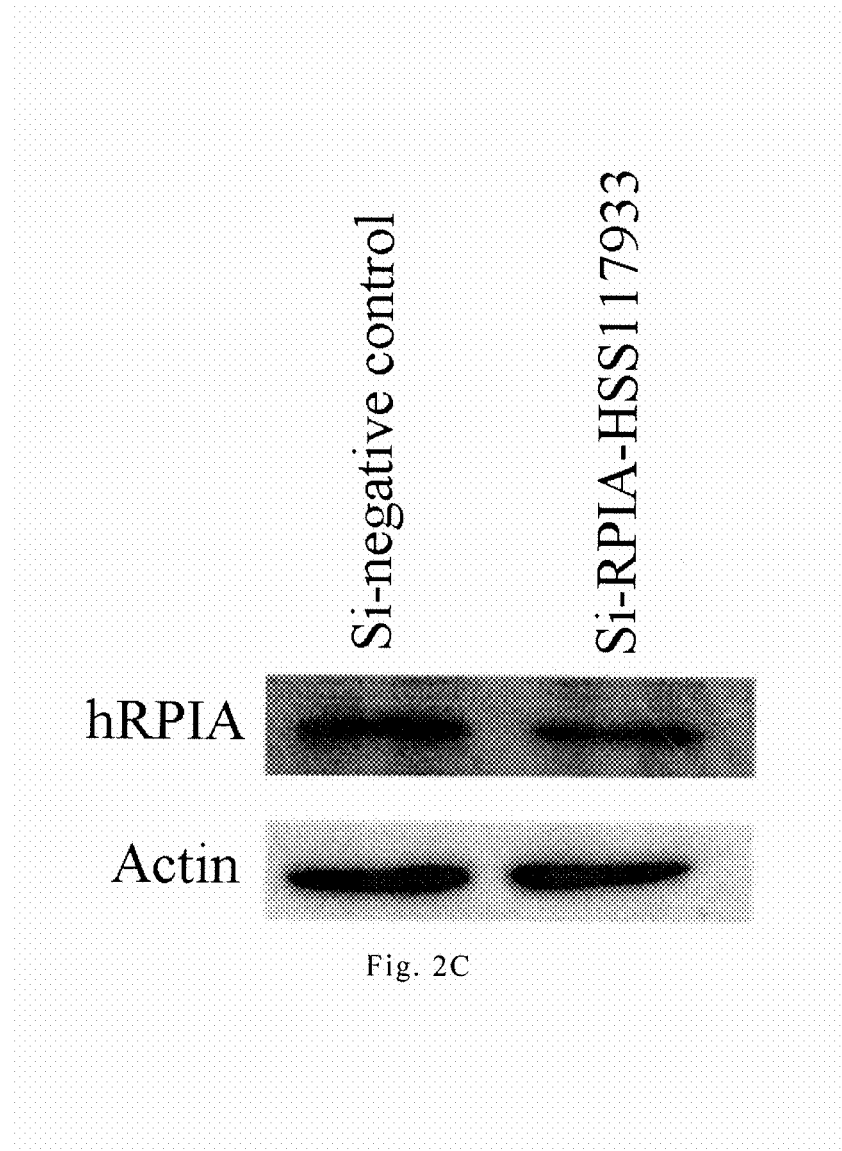
FIG. 2C shows the western blot analysis indicates that knockdown of hRPIA by siRNA, si-hRPIA-HSS117933 in HepG2 liver cancer cells results in reduced hRPIA expression. Actin was used as an internal control.

To examine whether the knockdown of hRPIA in cancer cells reduces cell growth, we used specific siRNA to knock down hRPIA expression. To quantify the cancer cell survival rate under the treatment of siRNA against hRPIA which sequence is: UUCACUUCACUCCAUUUGUGUACCC (SEQ NO. 1) and; GGGUACACAAAUG-GAGUGAAGUGAA (SEQ NO. 2), we perform western blot to examine the protein level of hRPIA in Hep3B, PLC5 and HepG2 which were treated with siRNA-hRPIA (cultured in 10% fetal bovine serum with DMEM in 37☐, 5% $CO_2$ for 48 hours respectively) as shown in FIG. 2A, FIG. 2B and FIG. 2C respectively. As shown in the figs, the protein level of hRPIA in the cancer cells is lower after adding siRNA.

Figure 3A:
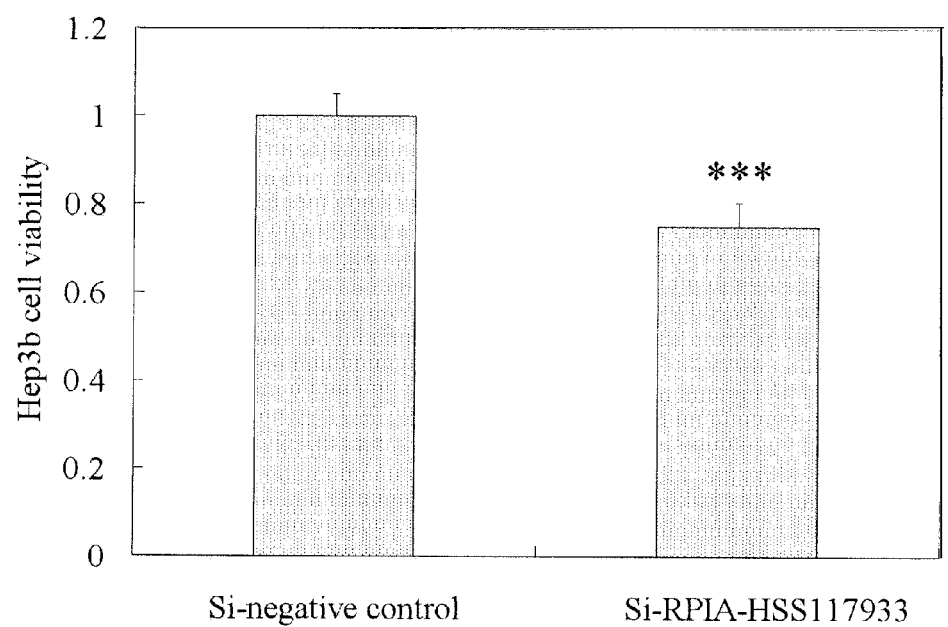
FIGS. 3A-C show the transfection of the liver cancer cells Hep3B (A), PLC5 (B), and HepG2 (C) with siRNA (20 nM si-hRPIA-HSS117933) to knockdown hRPIA results in significantly reduced cell viability in the liver cancer cell lines by MTT assay.
Figure 3B:
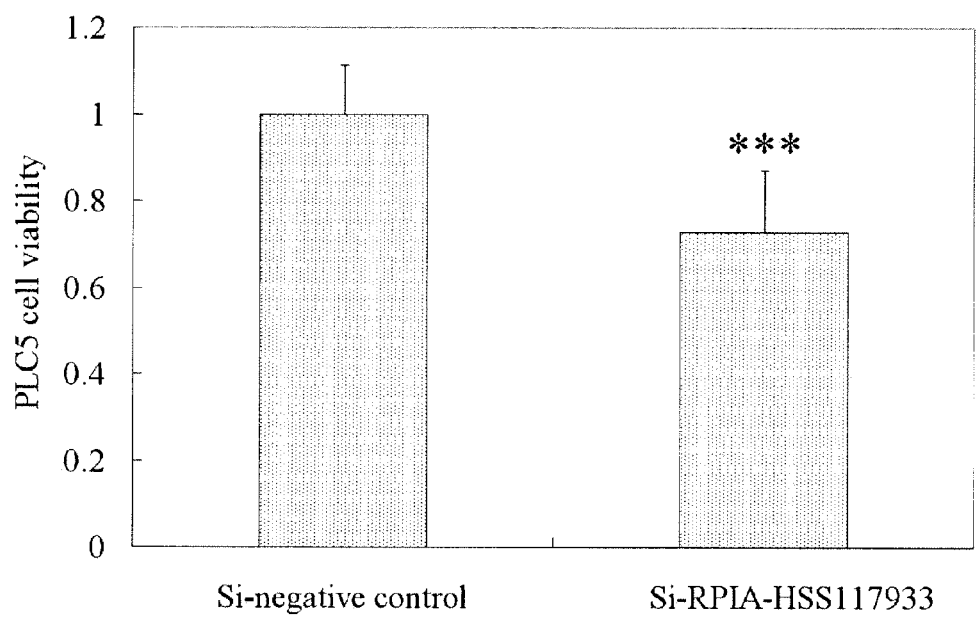
Figure 3C:
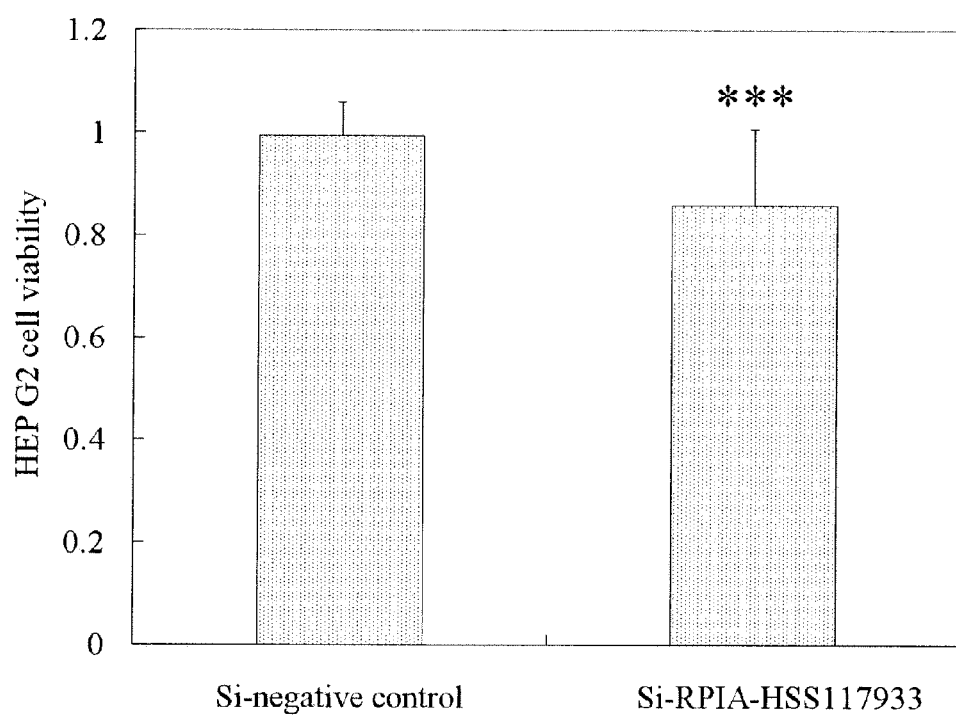

Further, we used 3-(4,5-dimethylthiazol-2-yl)-2,5-diphenyltetrazolium bromide (MTT) assay to examine whether the knockdown of hRPIA reduces cancer cell viability. As shown in FIG. 3A, the transfection of Hep3B cells with siRNA against hRPIA resulted in a significant reduction in cell viability. A similar data was obtained in PLC5 and HepG2 (FIG. 3B and FIG. 3C respectively).

As shown above, the cell viability is decreased after knockdown of hRPIA in hepatic cancer cell line.

Example 3

Examine the Cell Growth of Colon Cancer Cell after Knockdown of hRPIA

Figure 4B:
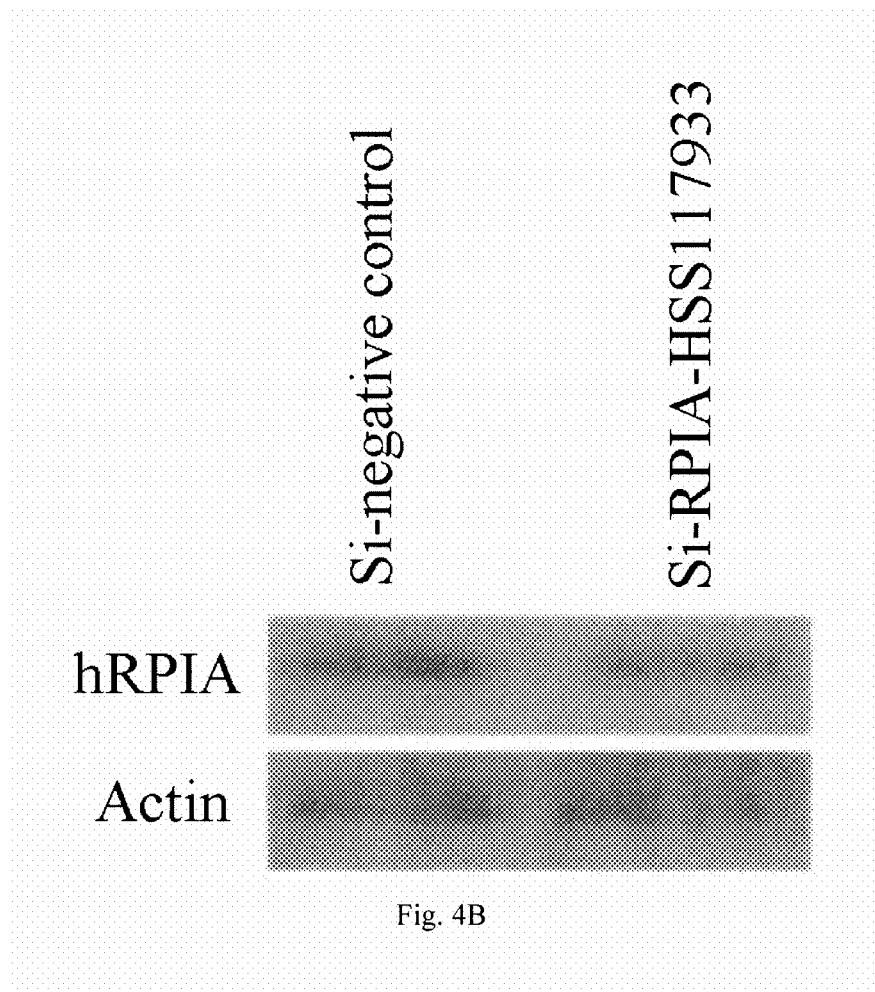

To examine whether the knockdown of hRPIA in cancer cells reduces cell growth, we used specific siRNA to knockdown hRPIA expression. To quantify the cancer cell survival rate under the treatment of siRNA against hRPIA which sequence is: UUCACUUCACUCCAUUUGUGUACCC (SEQ NO. 1) and; GGGUACACAAAUG-GAGUGAAGUGAA (SEQ NO. 2), we perform western blot to examine the protein level of hRPIA in SW480 and SW620 which were treated with siRNA-hRPIA (cultured in 10% fetal bovine serum with DMEM in 37☐, 5% $CO_2$ for 48 hours respectively) as shown in FIG. 4A and FIG. 4B respectively. As shown in the figs, the protein level of hRPIA in the cancer cells is lower after adding siRNA.

Figure 5A:
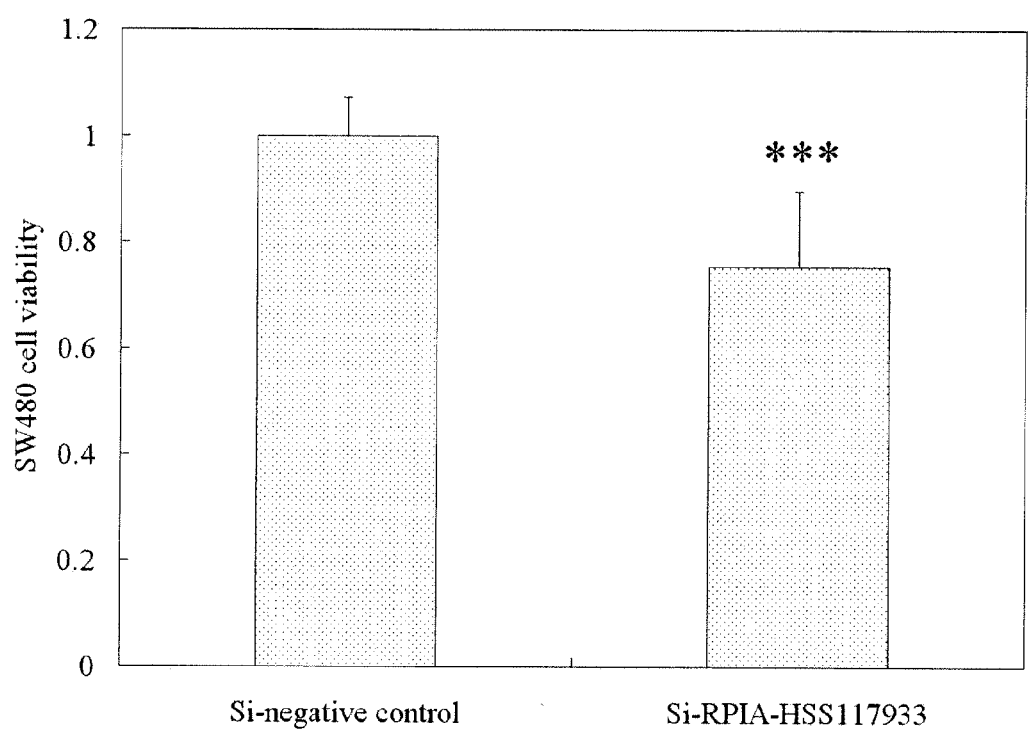
FIGS. 5A-B show the transfection of the colon cancer cells with siRNAs (20 nM) against hRPIA results in significantly reduced cell viability by MTT assay in the colon cancer cell lines SW480 (A) and SW620 (B).
Figure 5B:
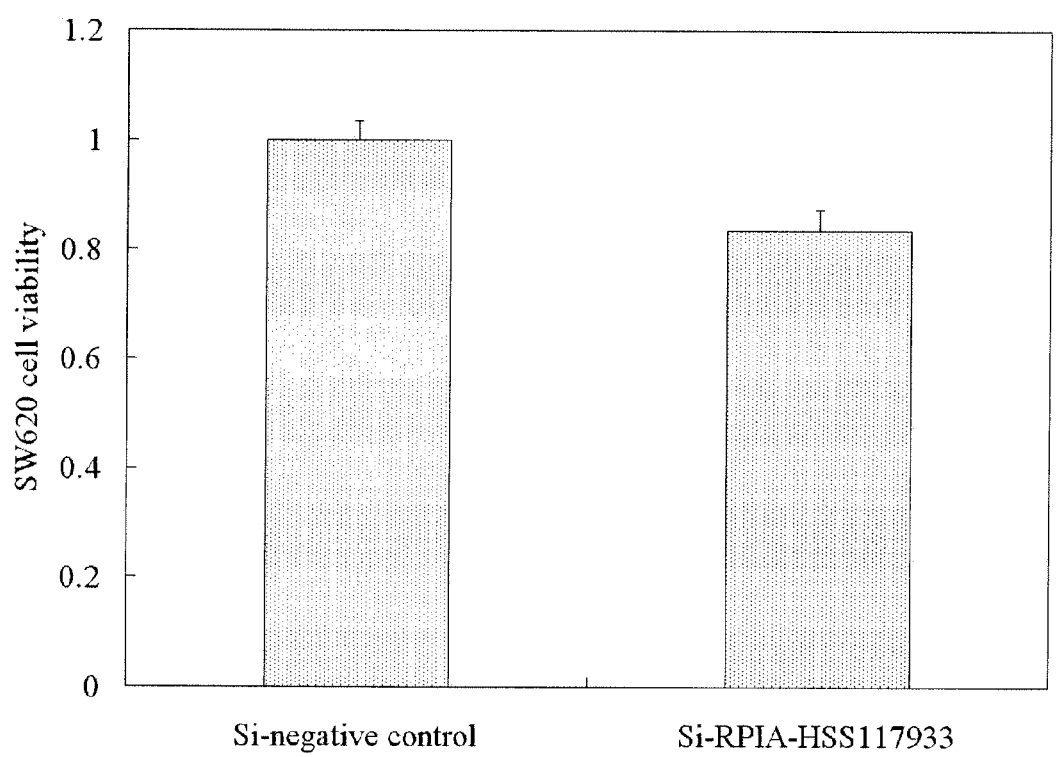

Further, we used 3-(4,5-dimethylthiazol-2-yl)-2,5-diphenyltetrazolium bromide (MTT) assay to examine whether the knockdown of hRPIA reduces cancer cell viability. As shown in FIG. 5A, the transfection of SW480 cells with siRNA against hRPIA resulted in a significant reduction in cell viability. A similar data was obtained in SW620 (FIG. 5B).

As shown above, the cell viability is decreased after knockdown of hRPIA in colon cancer cell line.

Example 4

Examine the Cell Growth of Liver Cancer Cell after Over-Expression of hRPIA

Figure 6A:
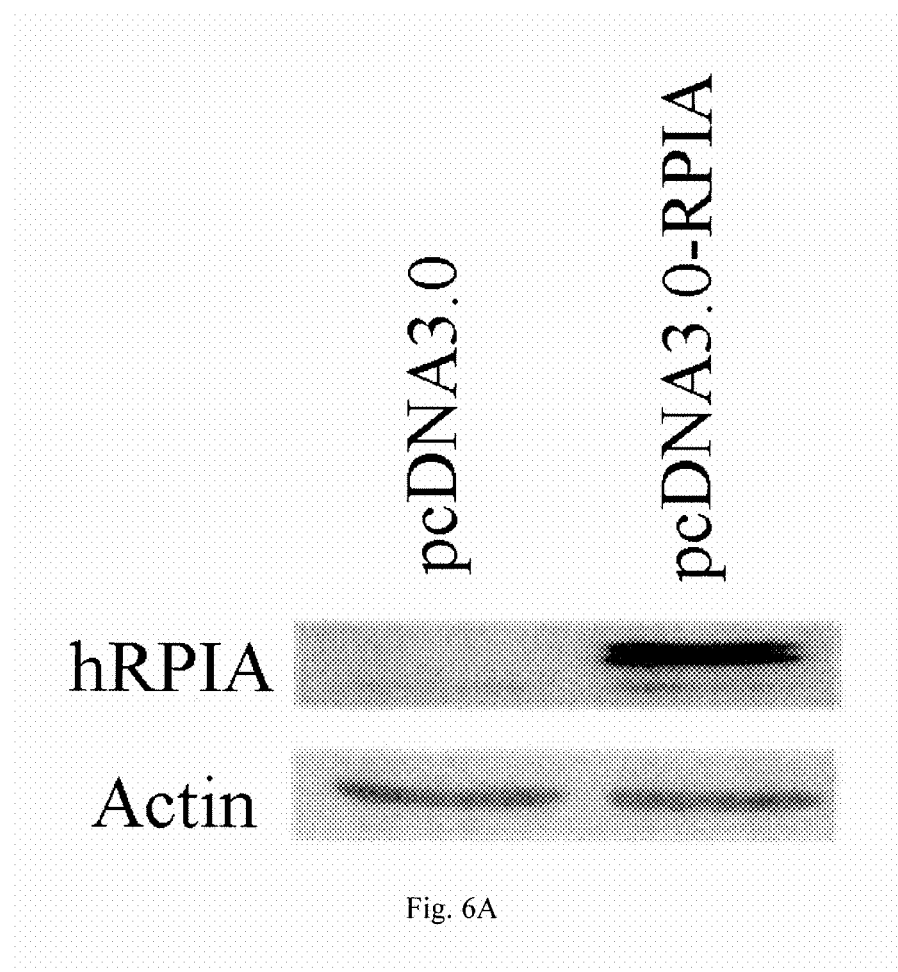
FIGS. 6A-C show the over-expression of hRPIA by the transfection of pcDNA3-hRPIA to Hep3B (A), PLC5 (B) and HepG2 (C) liver cancer cells results in elevated protein levels of hRPIA compared to the control cells by transfection of the vector (pcDNA3.0) only in the western blot.
Figure 6B:
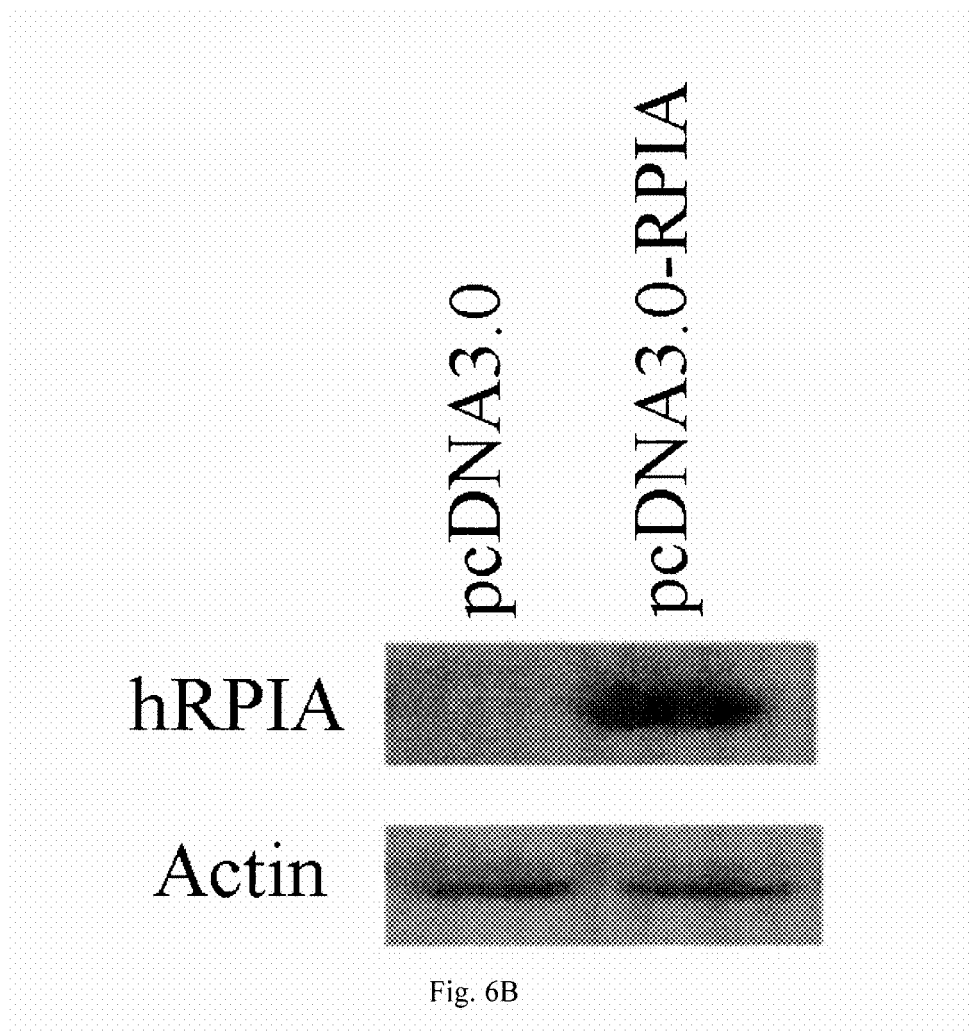
Figure 6C:
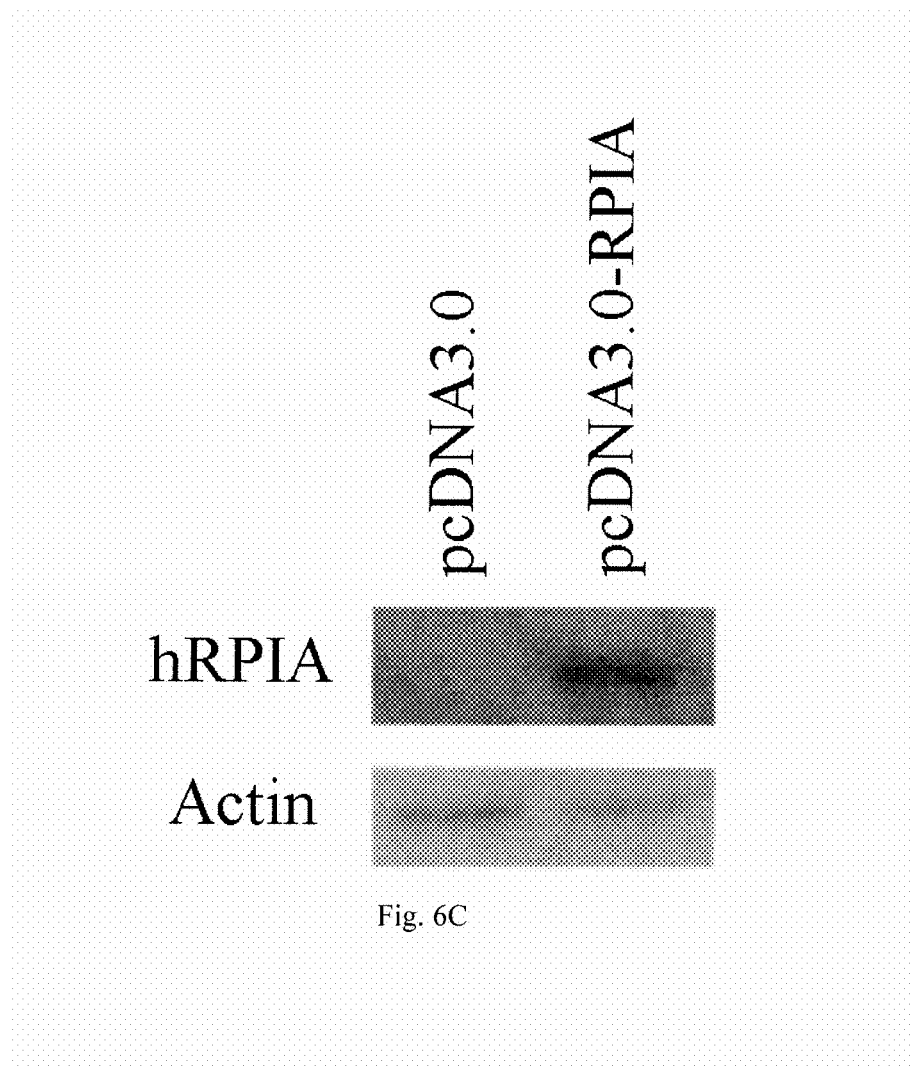

To examine whether the over-expression of hRPIA in cancer cells induces cell growth, we used pcDNA3-RPIA to over-express the hRPIA in Hep3B, PLC5 and HepG2 and used western blot to examine the protein level of hRPIA, as shown in FIG. 6A, FIG. 6B and FIG. 6C respectively. The protein level of hRPIA in the cancer cells is higher after adding pcDNA3-RPIA.

Figure 7A:
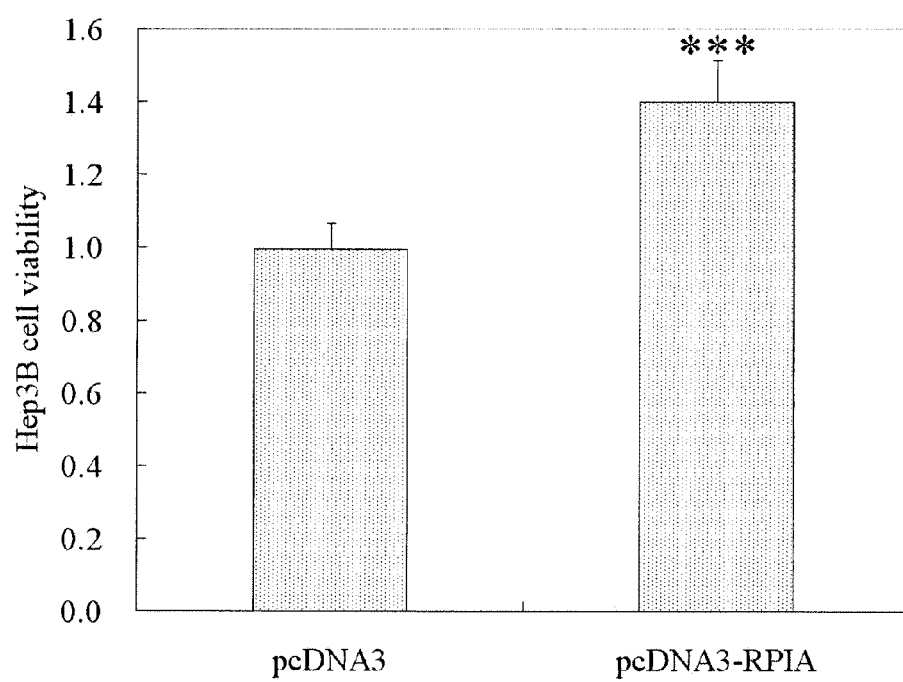
FIGS. 7A-C show the MTT proliferation assay shows that over-regulation of hRPIA promotes the cell viability in Hep3B (A), PLC5 (B), and HepG2 (C) liver cancer cells.
Figure 7B:
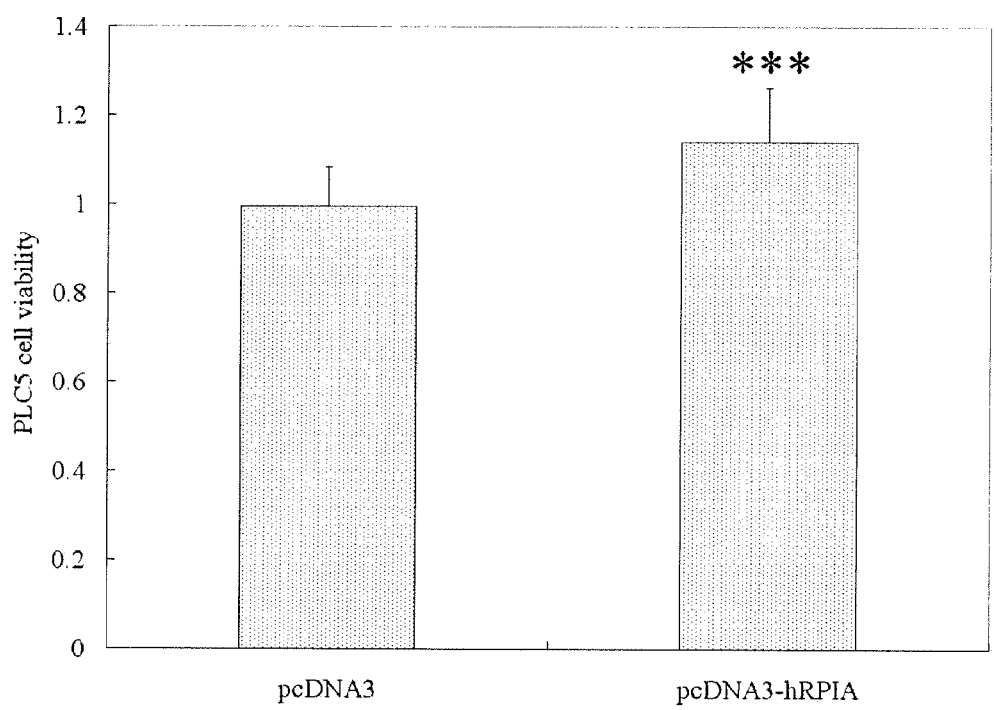
Figure 7C:
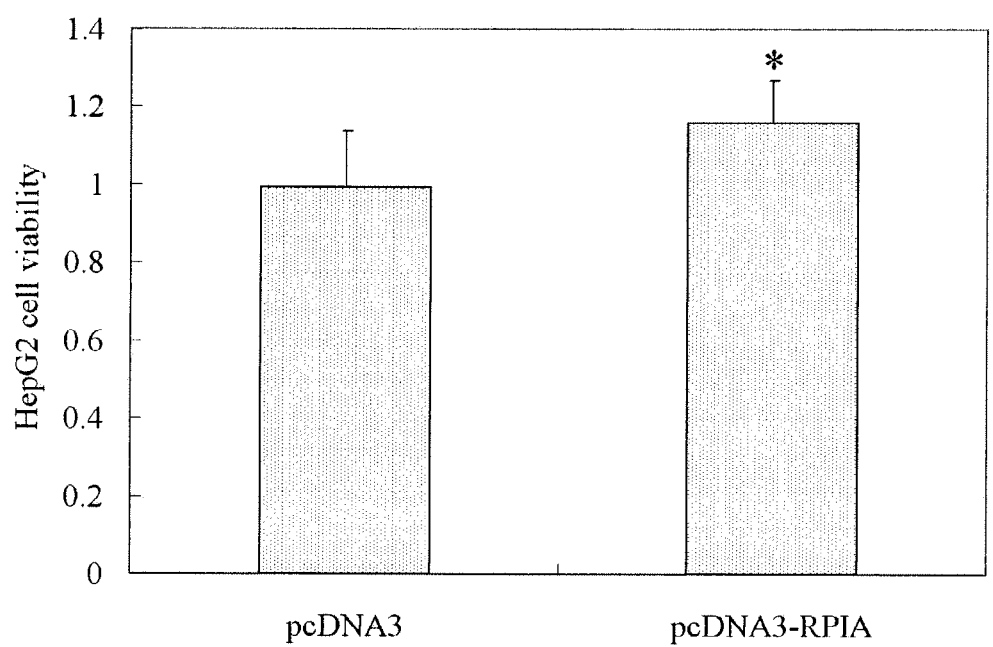

Further, we used 3-(4,5-dimethylthiazol-2-yl)-2,5-diphenyltetrazolium bromide (MTT) assay to examine whether the over-expression of hRPIA in cancer cells induces cancer cell viability. As shown in FIG. 7A, the cell viability is higher in Hep3B cells after adding pcDNA3-RPIA into cells. A similar data was obtained in PLC5 and HepG2 (FIG. 7B and FIG. 7C respectively).

As shown above, the cell viability is increased after over-expression of hRPIA in hepatic cancer cell line.

Example 5

Examine the Cell Growth of Colon Cancer Cell after Over-Expression of hRPIA

Figure 8A:
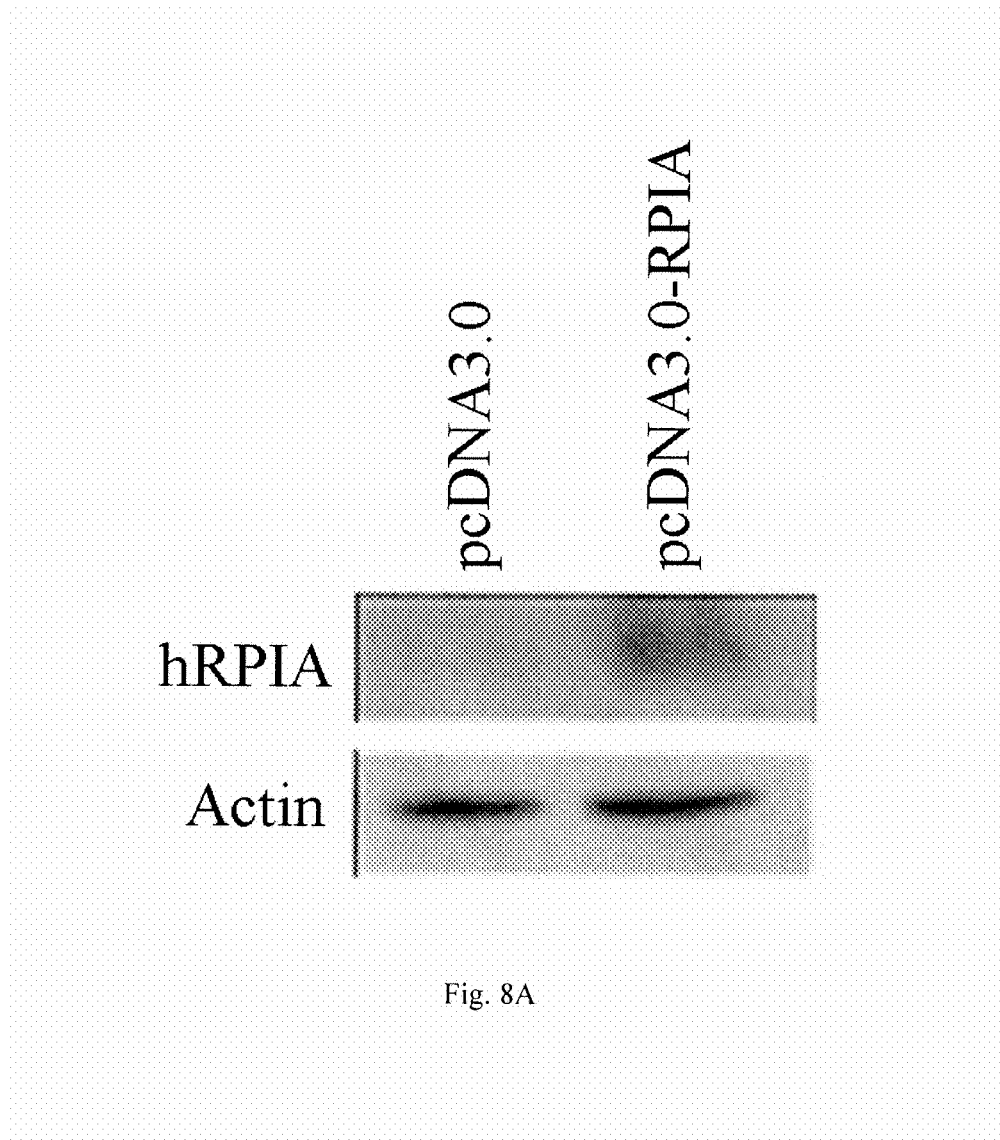
FIGS. 8A-B show the over-expression of hRPIA by the transfection of pcDNA3-hRPIA to SW480 (A) and SW620 (B) colon cancer cells results in elevated protein levels of hRPIA compared to the control cells by transfection of the vector (pcDNA3.0) only in the western blot.
Figure 8B:
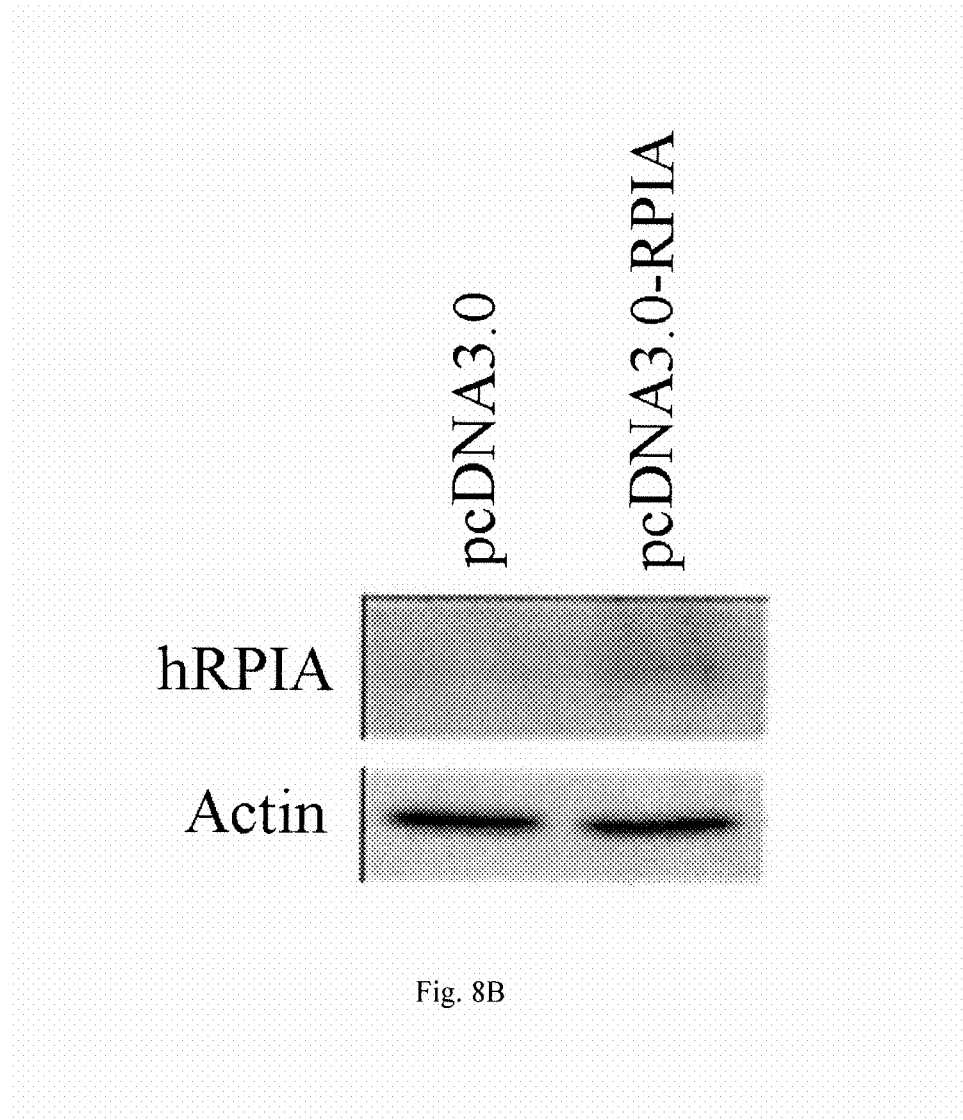

To examine whether the over-expression of hRPIA in cancer cells induces cell growth, we used pcDNA3-RPIA to over-express the hRPIA in SW480 and SW620 and used western blot to examine the protein level of hRPIA, as shown in FIG. 8A and FIG. 8B respectively. The protein level of hRPIA in the cancer cells is higher after adding pcDNA3-RPIA.

Figure 9A:
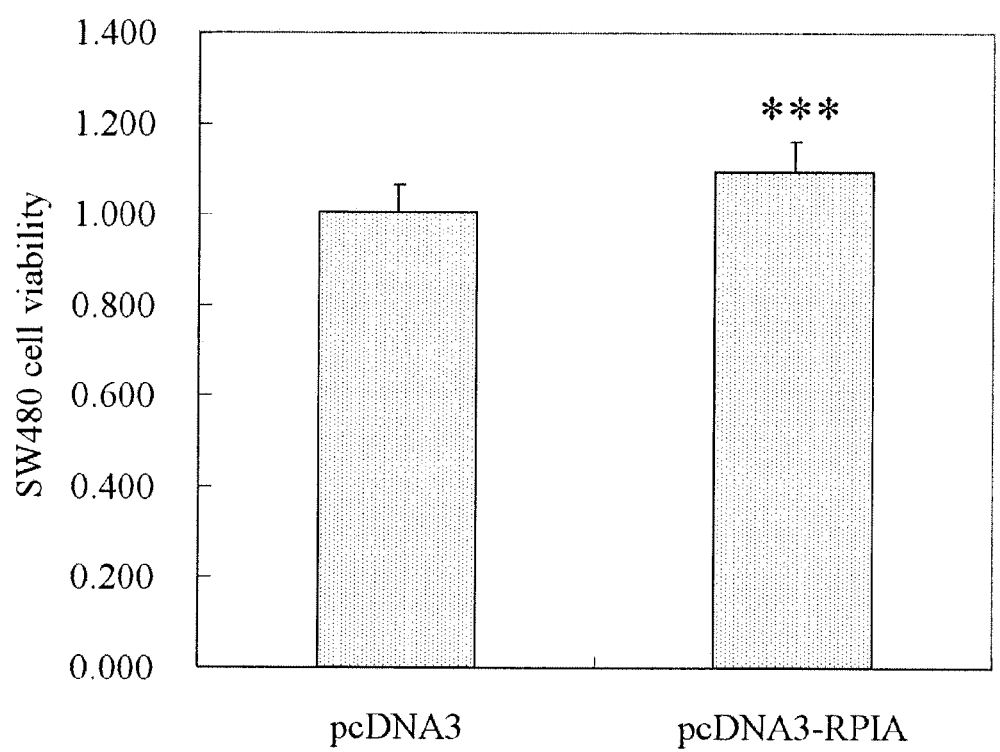
FIGS. 9A-B show the MTT proliferation assay shows that over-regulation of hRPIA enhances the cell viability in SW480 (A) and SW620 (B) colon cancer cells.
Figure 9B:
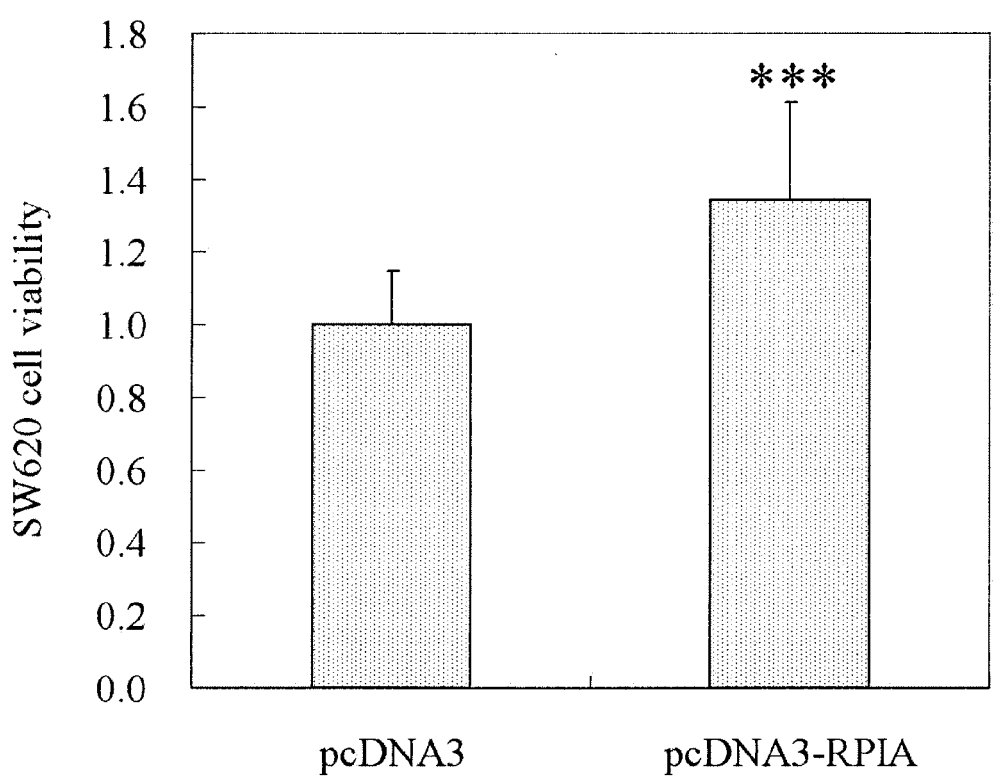

Further, we used 3-(4,5-dimethylthiazol-2-yl)-2,5-diphenyltetrazolium bromide (MTT) assay to examine whether the over-expression of hRPIA in cancer cells induces cancer cell viability. As shown in FIG. 9A, the cell viability is higher in SW480 cells after adding pcDNA3-RPIA into cells. A similar data was obtained in SW620 (FIG. 9B).

As shown above, the cell viability is increased after over-expression of hRPIA in colon cancer cell line.

Example 6

Figure 10A:
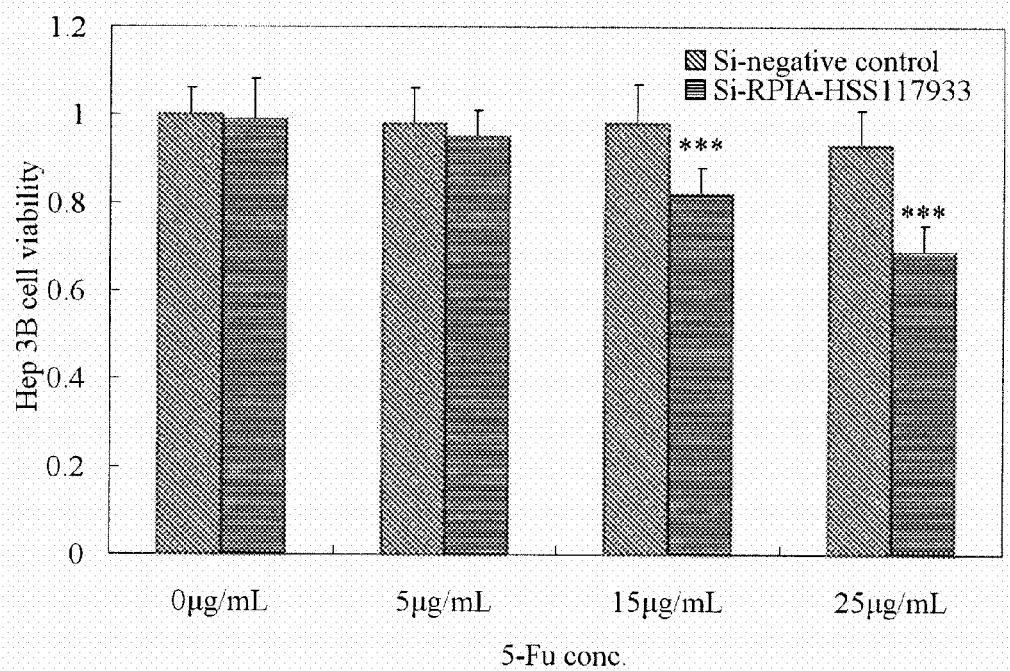
FIGS. 10A-C show the knockdown of hRPIA protein expression by siRNA significantly enhances the cytotoxicity by fluorouracil (0, 5, 15, 25 µg) treatment in Hep3B (A), PLC5 (B), and HepG2 (C) liver cancer cells.
Figure 10B:
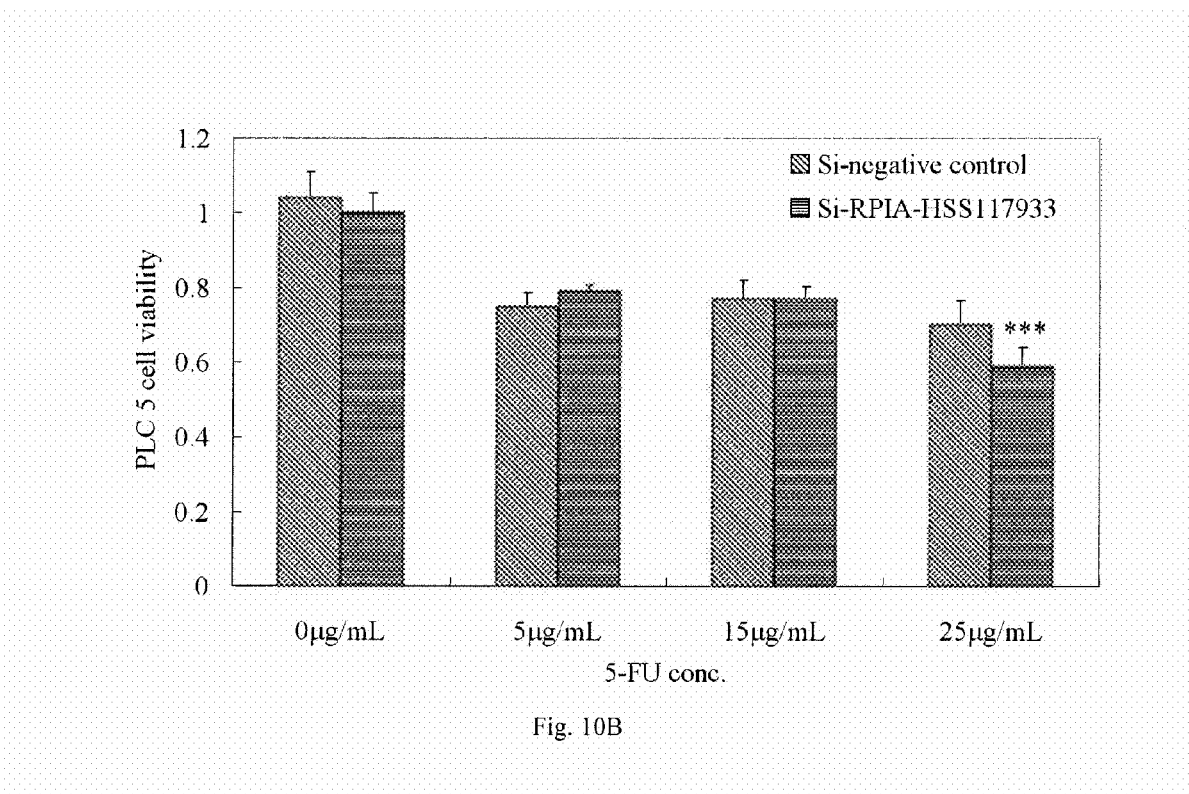
Figure 10C:
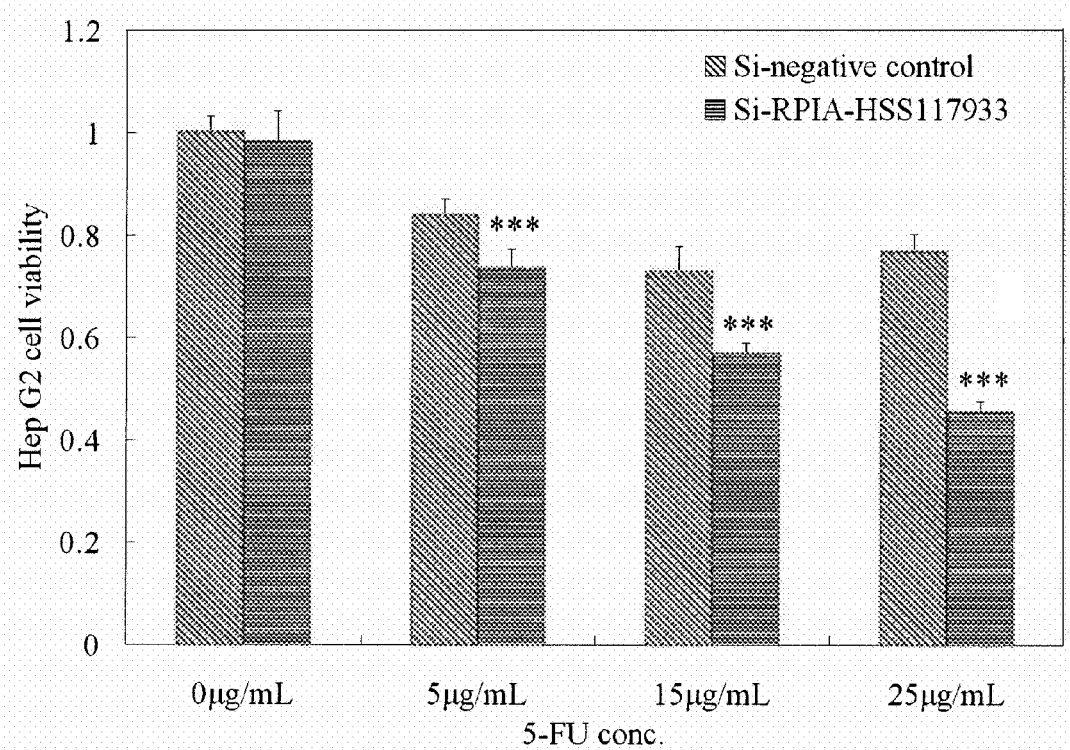

Examine the Influence of Chemotherapeutic Agents on Cell Growth of Liver Cancer Cell after Knocking Down of hRPIA To examine the influence of chemotherapeutic agents on cell growth of liver cancer cell after knocking down of hRPIA, we used specific siRNA to knockdown hRPIA expression and then added 5-fluorouracil (5-FU) by 0, 5, 15, 25 µg/mL into Hep3B, PLC5 and HepG2. Further, we used 3-(4,5-dimethylthiazol-2-yl)-2,5-diphenyltetrazolium bromide (MTT) assay to examine whether the over-expression of hRPIA in cancer cells induces cancer cell viability. As shown in FIGS. 10A, 10B and 10C respectively, suppression of hRPIA protein expression by si-hRPIA RNA significantly enhanced the cytotoxicity caused by 5-fluorouracil treatment in Hep3B, PLC5 and HepG2 cells as compared to si-negative control transfected cells.

As shown above, after knocking down of hRPIA in hepatic cancer cell line, the cell is easier to be killed by chemotherapeutic agents.

Example 7

Figure 11A:
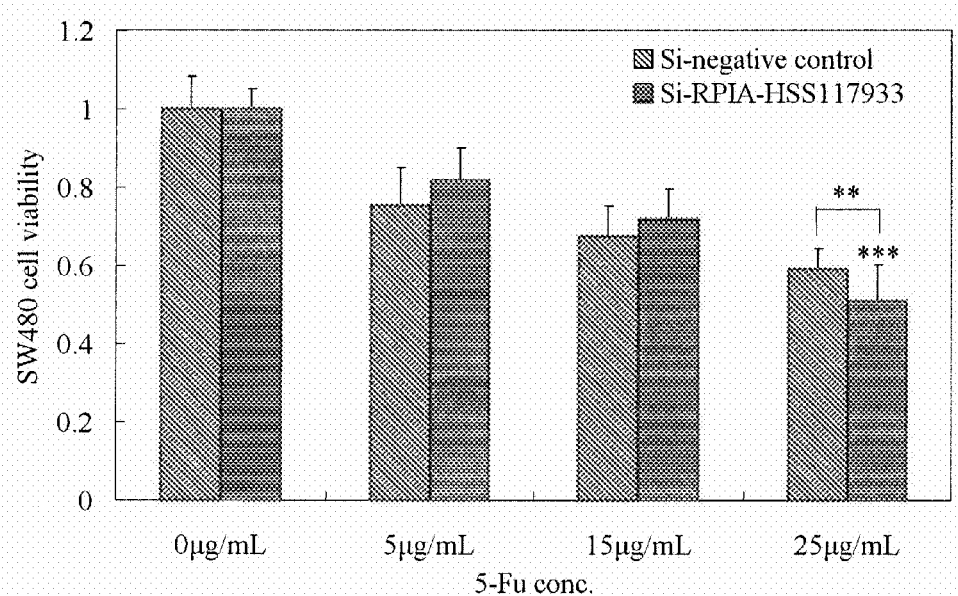
FIGS. 11A-B show the down-regulation of hRPIA protein expression by si-hRPIA RNA significantly enhanced the cytotoxicity caused by fluorouracil (0, 5, 15, 25 µg) treatment in SW480 (A) and SW620 (B) colon cancer cells.
Figure 11B:
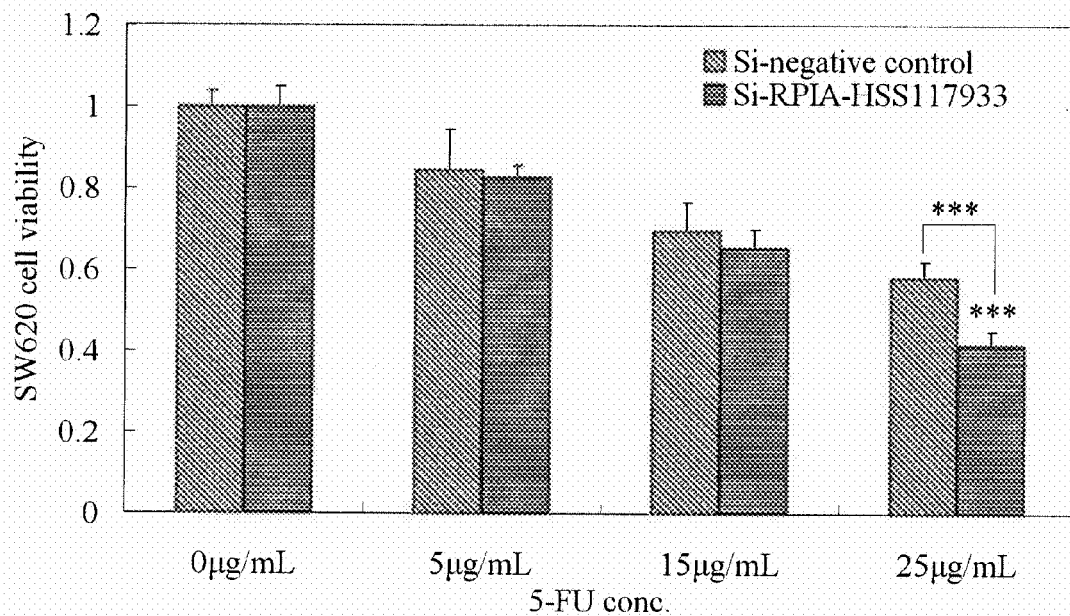

Examine the Influence of Chemotherapeutic Agents on Cell Growth of Colon Cancer Cell after Knocking Down of hRPIA To examine the influence of chemotherapeutic agents on cell growth of colon cancer cell after knocking down of hRPIA, we used specific siRNA to knock down hRPIA expression and then added 5-fluorouracil (5-FU) by 0, 5, 15, 25 µg/mL into SW480 and SW620. Further, we used 3-(4,5-dimethylthiazol-2-yl)-2,5-diphenyltetrazolium bromide (MTT) assay to examine whether the over-expression of hRPIA in cancer cells induces cancer cell viability. As shown in FIGS. 11A and 11B respectively, suppression of hRPIA protein expression by si-hRPIA RNA significantly enhanced the cytotoxicity caused by 5-fluorouracil treatment in SW480 and SW620 cells as compared to si-negative control transfected cells.

As shown above, after knocking down of hRPIA in colon cancer cell line, the cell is easier to be killed by chemotherapeutic agents.

Example 8

Examine the Cell Motility of Liver Cancer Cell after Knockdown of hRPIA

Figure 12:
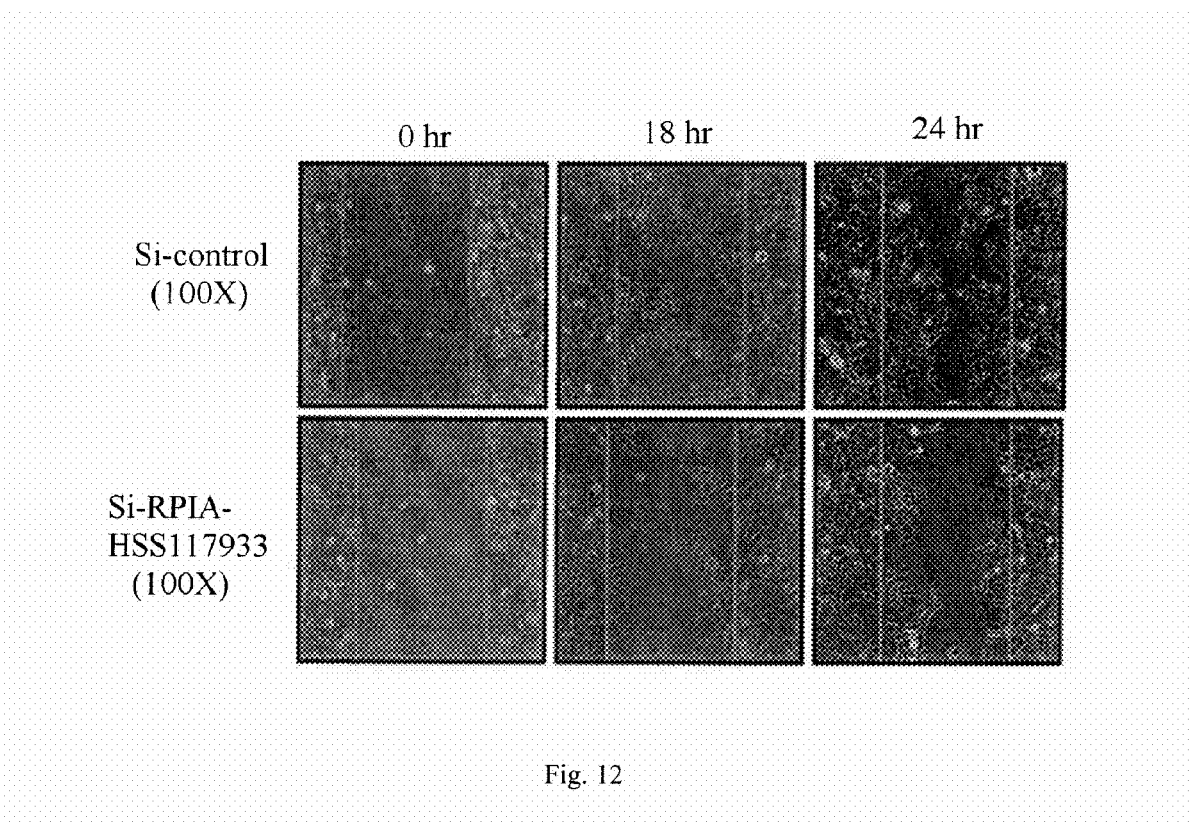
FIG. 12 shows the examination result of cell motility following hRPIA siRNA knockdown in hepatic cancer cells.

To examine whether the knockdown of hRPIA in cancer cells reduces cell motility, we used specific siRNA to knock down hRPIA expression. To quantify the cancer cell survival rate under the treatment of siRNA against hRPIA which sequence is: UUCACUUCACUCCAUUUGUGUACCC (SEQ NO. 1) and; GGGUACACAAAUG-GAGUGAAGUGAA (SEQ NO. 2) for 0, 18 and 24 hours, we perform wound healing assay to examine the cell motility of hRPIA in Hep3B which were treated with siRNA-hRPIA (cultured in 10% fetal bovine serum with DMEM in 37° C., 5% $CO_2$ for 48 hours) as shown in FIG. 12 respectively. As shown in the figs, the cell motility is lower after adding siRNA.

As shown above, the cell motility is decreased after knockdown of hRPIA in hepatic cancer cell line.

Example 9

Examine the Cell Motility of Colon Cancer Cell after Knockdown of hRPIA

Figure 13:
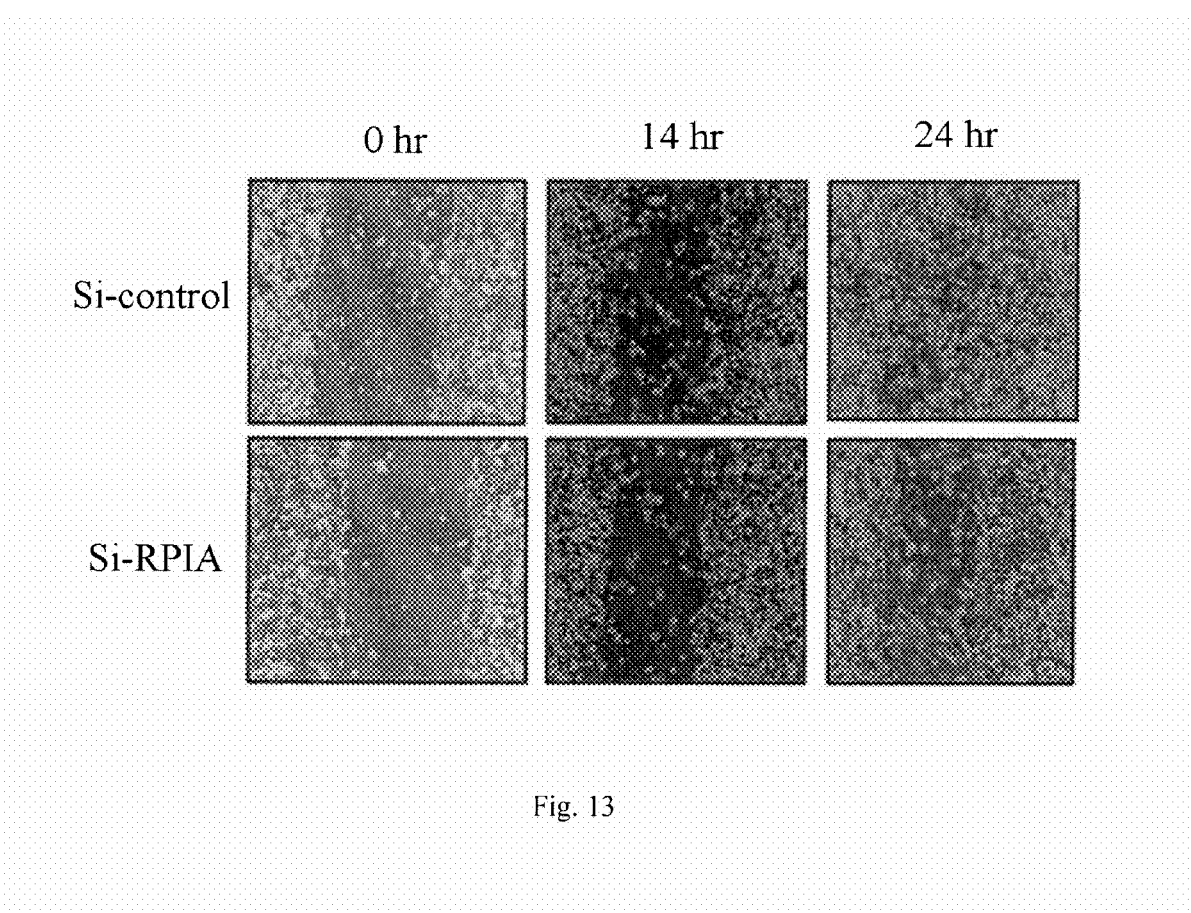
FIG. 13 shows the examination result of cell motility following hRPIA siRNA knockdown in colon cancer cells.

To examine whether the knockdown of hRPIA in colon cancer cells reduces cell motility, we used specific siRNA to knock down hRPIA expression. To quantify the cancer cell survival rate under the treatment of siRNA against hRPIA which sequence is: UUCACUUCACUCCAUUUGUGUACCC (SEQ NO. 1) and; GGGUACACAAAUGGAGUGAAGUGAA (SEQ NO. 2) for 0, 14 and 24 hours, we perform wound healing assay to examine the cell motility of hRPIA in SW480 which were treated with siRNA-hRPIA (cultured in 10% fetal bovine serum with DMEM in 37□, 5% $CO_2$ for 48 hours) as shown in FIG. 13 respectively. As shown in the figs, the cell motility is lower after adding siRNA.

As shown above, the cell motility is decreased after knockdown of hRPIA in colon cancer cell line.

Example 10

Figure 14A:
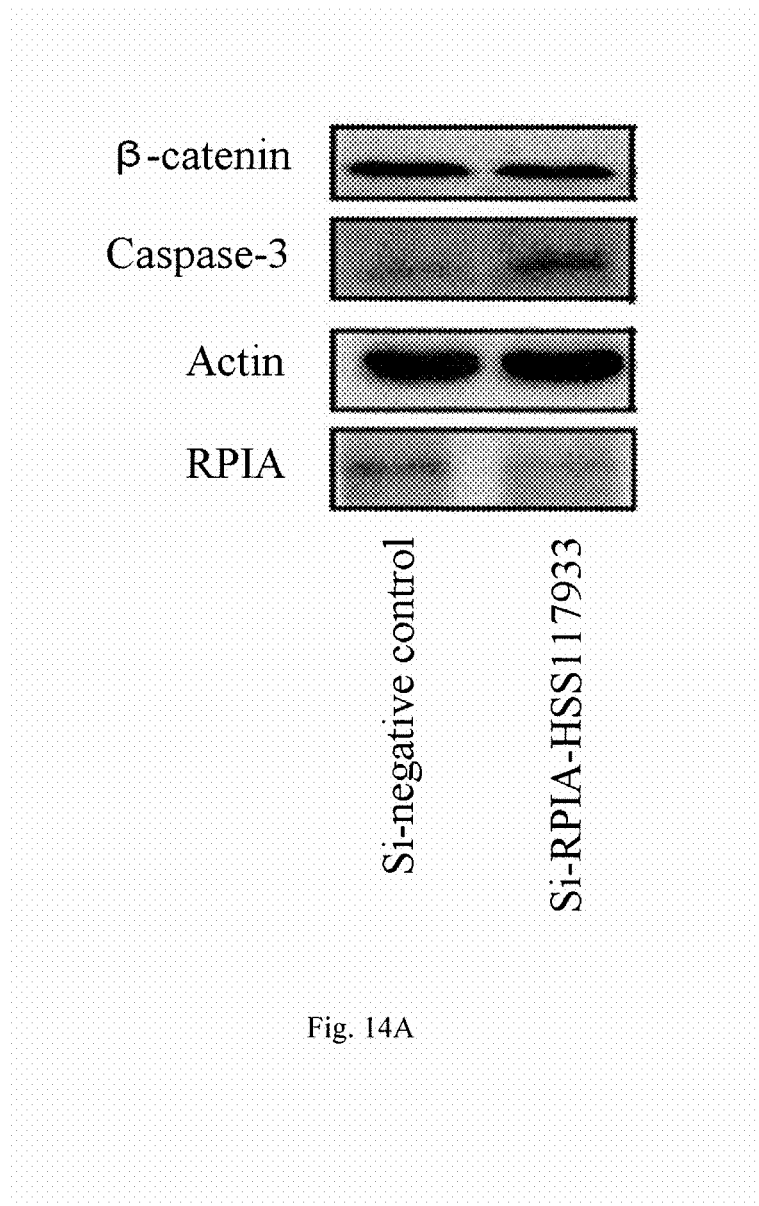
FIGS. 14A-C shows the knockdown of hRPIA by siRNA increases caspase-3 expression and decreases β-catenin expression in Hep3B (A), PLC5 (B), and HepG2 (C) liver cancer cells.
Figure 14B:
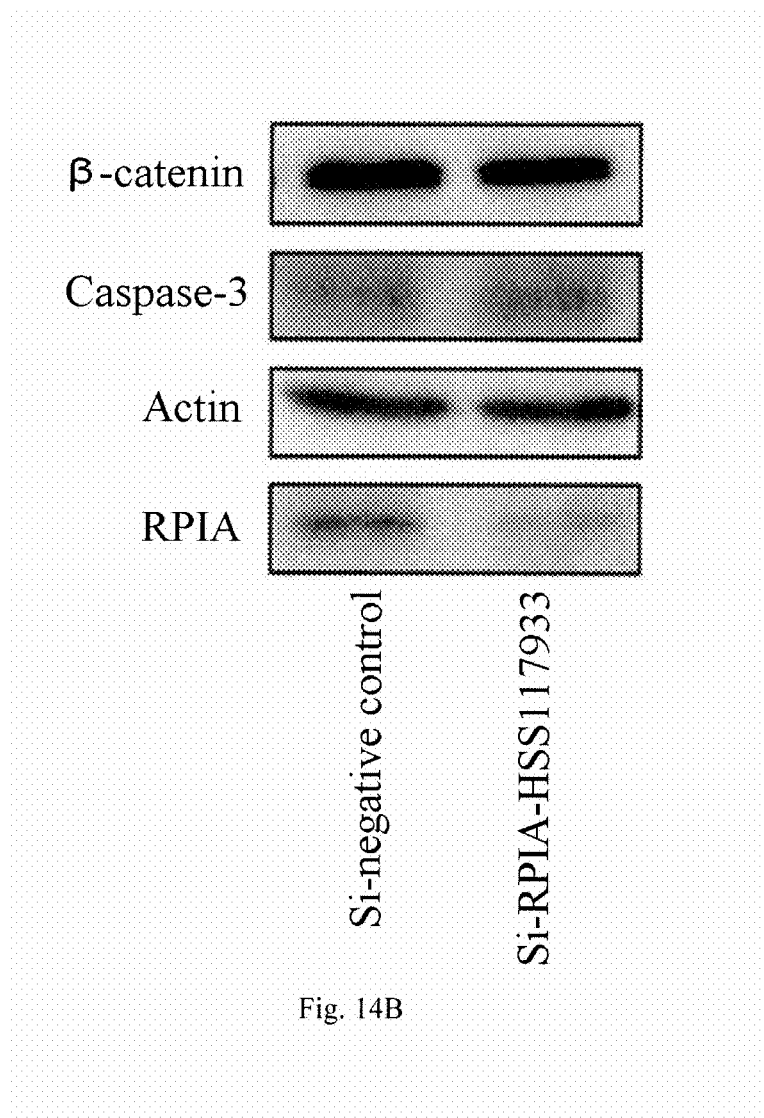
Figure 14C:
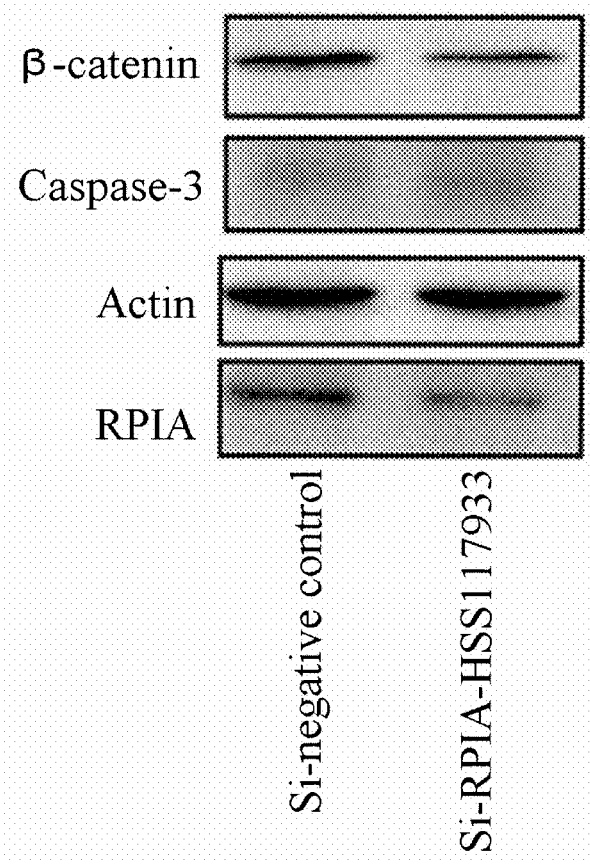

Examine the Influence of hRPIA on β-Catenin and Caspase-3 Protein Expression of Liver Cancer Cells To examine whether the knockdown of hRPIA in hepatic cancer cells induces cell apoptosis, we used specific siRNA which sequence is: UUCACUUCACUCCAUUUGUGUACCC (SEQ NO. 1) and; GGGUACACAAAUGGAGUGAAGUGAA (SEQ NO. 2) to knock down hRPIA expression. Next, we used western blot to examine the protein level of caspase-3 and β-catenin. As shown in FIG. 14A, the transfection of Hep3B (cultured in 10% fetal bovine serum with DMEM in 37° C., 5% $CO_2$ for 48 hours) cells with siRNA against hRPIA resulted in an increased activity of caspase-3. A similar data was obtained in PLC5 and HepG2 (FIG. 14B and FIG. 14C respectively). In addition, in FIG. 14C, the transfection of HepG2 cells with siRNA against hRPIA resulted in a significant reduction of β-catenin protein level. However, the transfection of Hep3B and PLC5 cells with siRNA against hRPIA resulted in a slightly reduction of β-catenin protein level.

As shown above, after knocking down hRPIA expression, the protein level of β-catenin is decreased, which means the cell motility is decreased, and the protein level of caspase-3 is increased, which means the cell is going to apoptosis.

Example 11

Figure 15:
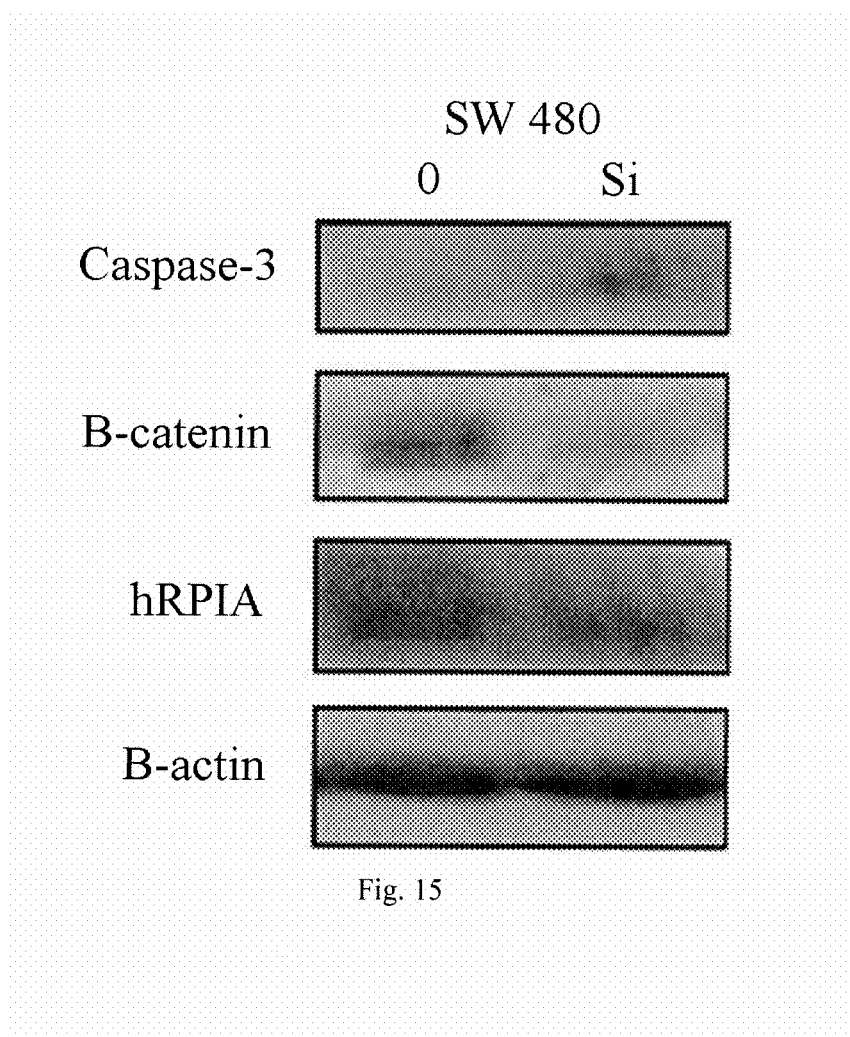
FIG. 15 shows the examination of caspase-3 and β-catenin protein level following hRPIA siRNA knockdown in colon cancer cells.

Examine the Influence of hRPIA on β-Catenin and Caspase-3 Protein Expression of Colon Cancer Cells To examine whether the knockdown of hRPIA in colon cancer cells induces cell apoptosis, we used specific siRNA which sequence is: UUCACUUCACUCCAUUUGUGUACCC (SEQ NO. 1) and; GGGUACACAAAUGGAGUGAAGUGAA (SEQ NO. 1) to knock down hRPIA expression. Next, we used western blot to examine the protein level of caspase-3 and β-catenin. As shown in FIG. 15, the transfection of SW480 which were treated with siRNA-hRPIA (cultured in 10% fetal bovine serum with DMEM in 37° C., 5% $CO_2$ for 48 hours) cells with siRNA against hRPIA resulted in an increased activity of caspase-3. In addition, the transfection of SW480 cells with siRNA against hRPIA resulted in a significant reduction of β-catenin protein level.

As shown above, after knocking down hRPIA expression, the protein level of β-catenin is decreased, which means the cell motility is decreased, and the protein level of caspase-3 is increased, which means the cell is going to apoptosis.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method for inducing the cancer cell apoptosis by the way of adding a siRNA to inhibiting the expression of ribose-5-phosphate isomerase A in said cancer cell, wherein said cancer cell is colon cancer cell or hepatic cancer cell.

2. The method of claim 1, wherein the way of inhibiting the expression of ribose-5-phosphate isomerase A is to knockdown a ribose-5-phosphate isomerase (RPI) gene in said cell.

3. A method for inhibiting the cancer cell migration by the way of adding a siRNA to inhibiting the expression of ribose-5-phosphate isomerase A in said cancer cell, wherein said cancer cell is colon cancer cell or hepatic cancer cell.

4. The method of claim 3, wherein the way of inhibiting the expression of ribose-5-phosphate isomerase A is to knockdown a ribose-5-phosphate isomerase (RPI) gene in said cell.

5. A method of enhancing the sensitivity of cancer cells to chemotherapeutic agents by the way of adding a siRNA to inhibiting the expression of ribose-5-phosphate isomerase A in said cancer cell, wherein said cancer cell is colon cancer cell or hepatic cancer cell.

* * * * *

SEQUENCE LISTING

```
<160> NUMBER OF SEQ ID NOS: 2

<210> SEQ ID NO 1
<211> LENGTH: 25
<212> TYPE: RNA
<213> ORGANISM: Artificial
<220> FEATURE:
<223> OTHER INFORMATION: hRPIA siRNA

<400> SEQUENCE: 1
uucacuucac uccauuugug uaccc                                         25

<210> SEQ ID NO 2
<211> LENGTH: 25
<212> TYPE: RNA
<213> ORGANISM: Artificial
<220> FEATURE:
<223> OTHER INFORMATION: hRPIA siRNA

<400> SEQUENCE: 2
ggguacacaa auggagugaa gugaa                                         25
```